(12) United States Patent
Martin

(10) Patent No.: US 10,446,049 B2
(45) Date of Patent: Oct. 15, 2019

(54) PHYSICAL TRAINING SYSTEM AND METHOD

(71) Applicant: Kevin L. Martin, Memphis, TN (US)

(72) Inventor: Kevin L. Martin, Memphis, TN (US)

( * ) Notice: Subject to any disclaimer, the term of this patent is extended or adjusted under 35 U.S.C. 154(b) by 325 days.

(21) Appl. No.: 13/780,910

(22) Filed: Feb. 28, 2013

(65) Prior Publication Data

US 2013/0224708 A1  Aug. 29, 2013

Related U.S. Application Data

(60) Provisional application No. 61/604,417, filed on Feb. 28, 2012.

(51) Int. Cl.
| | |
|---|---|
| *G09B 19/00* | (2006.01) |
| *A63B 71/06* | (2006.01) |
| *A63F 13/214* | (2014.01) |
| *A63B 21/00* | (2006.01) |
| *A63B 23/04* | (2006.01) |

(52) U.S. Cl.
CPC .......... *G09B 19/00* (2013.01); *A63B 71/0622* (2013.01); *G09B 19/0038* (2013.01); *A63B 21/4037* (2015.10); *A63B 23/0458* (2013.01); *A63F 13/214* (2014.09); *A63F 2300/1068* (2013.01); *A63F 2300/8047* (2013.01)

(58) Field of Classification Search
CPC ... A63B 5/00; A63B 71/0622; A63B 21/4037; A63B 23/0458; A63F 13/214; A63F 2300/1068; A63F 2300/8047; G09B 19/0038; G09B 19/00
USPC .................................................. 434/247, 258
See application file for complete search history.

(56) References Cited

U.S. PATENT DOCUMENTS

| | | | |
|---|---|---|---|
| 4,261,563 | A | 4/1981 | Goldfarb |
| 4,699,221 | A | 10/1987 | Malinowski et al. |
| 5,277,674 | A | 1/1994 | Tsuchiya et al. |
| 5,401,224 | A | 3/1995 | Tsuchiya et al. |
| 5,469,740 | A | 11/1995 | French et al. |
| 5,491,912 | A | 2/1996 | Snabb et al. |
| 5,584,779 | A | 12/1996 | Knecht et al. |
| 5,720,200 | A | 2/1998 | Anderson et al. |
| 5,752,330 | A | 5/1998 | Snabb |
| 5,838,638 | A | 11/1998 | Tipton et al. |
| 5,916,046 | A | 6/1999 | Allred et al. |
| 6,110,073 | A | 8/2000 | Saur et al. |
| 6,181,467 | B1 | 1/2001 | Tipton et al. |
| 6,336,891 | B1 * | 1/2002 | Fedrigon ............ A63B 24/0006 482/8 |
| 6,685,480 | B2 * | 2/2004 | Nishimoto et al. ........... 434/247 |

(Continued)

OTHER PUBLICATIONS

Galpin, A 4-Week Choice Foot Speed and Choice Reaction Training Program Improves Agility in Previously Non-Agility Trained, but Active Men and Women, Journal of Strength and Conditioning Research, Nov. 2008, pp. 1901-1907, vol. 22.

*Primary Examiner* — Jack Yip

(57) ABSTRACT

Systems, methods, and computer-readable media for providing a physical training routine for a user are disclosed. One such method may include displaying a visual indicator indicating a movement to be completed by the user and determining whether the user completes the movement. The methods also include recording one or more characteristics of the movement and providing feedback to the user based on the one or more characteristics.

18 Claims, 6 Drawing Sheets

(56) References Cited

U.S. PATENT DOCUMENTS

| | | | |
|---|---|---|---|
| 7,060,000 B2 * | 6/2006 | Carlson | A63B 69/0053 434/250 |
| 7,270,628 B2 | 9/2007 | Campanaro et al. | |
| 7,500,260 B2 | 3/2009 | Lupoi et al. | |
| 7,513,852 B2 | 4/2009 | Wilkins et al. | |
| 7,572,206 B2 | 8/2009 | Wilkins et al. | |
| 7,604,570 B2 | 10/2009 | Wilkins et al. | |
| 7,604,571 B2 | 10/2009 | Wilkins et al. | |
| 8,253,586 B1 | 8/2012 | Matak | |
| 8,727,885 B2 * | 5/2014 | Berger | A63F 13/10 273/243 |
| 8,827,815 B2 | 9/2014 | Burroughs et al. | |
| 8,860,584 B1 | 10/2014 | Matak | |
| 8,957,785 B1 | 2/2015 | Matak et al. | |
| 9,017,222 B2 | 4/2015 | Hofeldt et al. | |
| 9,326,911 B2 | 5/2016 | Wyatt et al. | |
| 9,429,411 B2 | 8/2016 | Meschter et al. | |
| 9,456,785 B1 | 10/2016 | Matak et al. | |
| 9,553,873 B2 | 1/2017 | Agnew et al. | |
| 2001/0016510 A1 * | 8/2001 | Ishikawa | A63F 13/10 463/7 |
| 2005/0153265 A1 * | 7/2005 | Kavana | G09B 19/0015 434/250 |
| 2006/0258512 A1 * | 11/2006 | Nicolas et al. | 482/52 |
| 2006/0266200 A1 * | 11/2006 | Goodwin | A63F 13/02 84/611 |
| 2007/0079690 A1 * | 4/2007 | Chiwata | G10H 1/348 84/609 |
| 2008/0004111 A1 * | 1/2008 | Prather | A63F 13/06 463/36 |
| 2008/0102991 A1 * | 5/2008 | Hawkins | A63B 69/0053 473/422 |
| 2008/0146329 A1 * | 6/2008 | Kodama | A63B 69/00 463/31 |
| 2009/0221372 A1 * | 9/2009 | Casey | A63F 13/06 463/36 |
| 2010/0204615 A1 * | 8/2010 | Kyle | A63B 24/0006 600/595 |
| 2012/0122588 A1 * | 5/2012 | Berger | A63F 13/80 463/42 |

\* cited by examiner

PHYSICAL TRAINING SYSTEM AND METHOD

RELATED APPLICATION

The present application claims priority to U.S. Provisional Patent Application No. 61/604,417, filed on Feb. 28, 2012, which is fully incorporated herein by reference.

TECHNICAL FIELD

The present disclosure relates to methods, systems, and computer-readable media for providing physical training. More particularly, the present disclosure relates to methods, systems, and computer-readable media for providing instant feedback and objective assessment of the effectiveness of the physical training.

BACKGROUND

In sports training, an athlete's training process is normally directed by a coach. The coach typically designs training sessions and monitors the athlete's performance. In this traditional framework, the assessment of an athlete's performance largely depends on the coach's experience, judgment, and patience. It is often difficult for the athlete to receive instant feedback from the coach. In addition, the feedback may not be based on objective measures. In physical therapy especially rehabilitation treatment, a physician often assesses a patient's condition based on overall physical appearance. Subtle imperfections, such as slight imbalance between injured and non-injured legs, are difficult to capture. Therefore, it is desirable to develop systems and methods for providing instant feedback and objective assessment of the effectiveness of physical training.

SUMMARY

Some disclosed embodiments may involve methods, systems, and computer-readable media for providing physical training to a user. One such system may include a memory for storing a set of instructions. The system may also include a processor communicatively connected to the memory. When executing the set of instructions, the processor may be configured to display a visual indicator on a display panel to indicating a movement to be completed by the user and determine whether the user completes the movement. Moreover, the processor may be configured to record one or more characteristics of the movement and provide feedback to the user based on the one or more characteristics.

The preceding summary is not intended to restrict in any way the scope of the claimed invention. In addition, it is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate various embodiments and exemplary aspects of the present invention and, together with the description, explain principles of the invention. In the drawings.

DESCRIPTION OF EXEMPLARY EMBODIMENTS

Reference will now be made in detail to exemplary embodiments of the invention, examples of which are illustrated in the accompanying drawings. When appropriate, the same reference numbers are used throughout the drawings to refer to the same or like parts.

Embodiments of the present disclosure may involve systems, methods, and computer readable media for providing physical training to a user. As used herein, physical training may include physical condition testing, sports training, physical therapy, athletic performance training, recreational exercise, or a general purpose workout, etc. The physical training may involve one or more physical movements of the body part(s) of the user, such as upper limbs, lower limbs, or whole body movements. A particular set of movements may be referred to as a "drill." During a training session, the user may perform one or more pre-set drills and/or customized drills. A customized drill may be built by the user from scratch. Alternatively, a customized drill may be modified from a pre-set drill.

Figure 1:
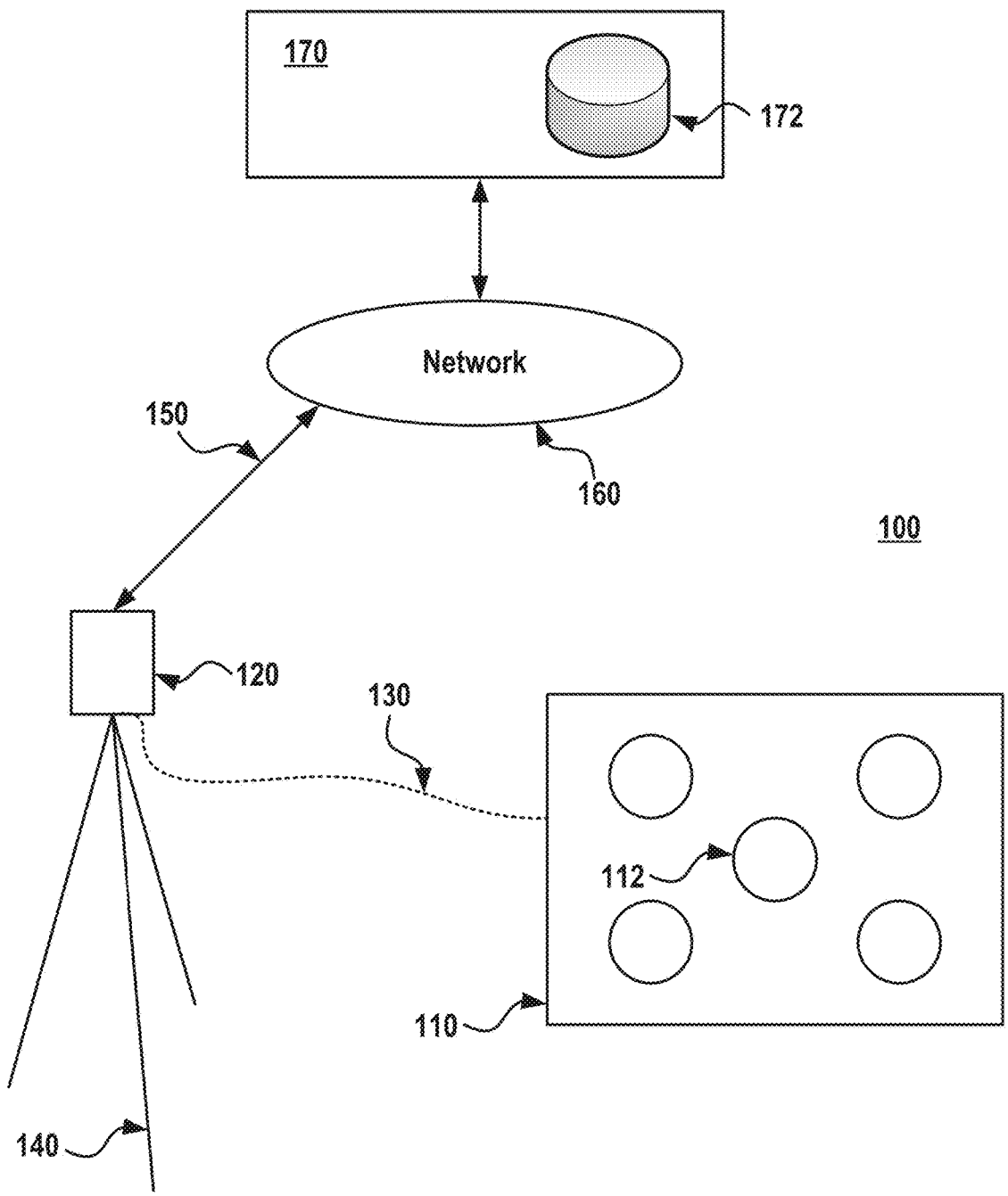
FIG. 1 is a schematic diagram of an exemplary physical training system, in accordance with some disclosed embodiments.

FIG. 1 illustrates an exemplary training system 100. Training system 100 may include a sensor pad 110. Sensor pad 110 may also be referred to as a touch board, a sensing board, etc. Sensor pad 110 may include one or more sensor units 112. Sensor unit 112 may sense applied pressure or force and provide signals indicating whether the sensor unit has been pressed or touched. In some embodiments, sensor unit 112 may also provide signals indicating the time duration of the pressure or force applied to the sensor unit 112.

Training system 100 may include a controller 120. Controller 120 may include a general-purpose portable computing device such as a tablet, a PDA, a mobile phone, a laptop, or any other suitable computing apparatus equipped with a physical training software application. in some embodiments, controller 120 may include a dedicated computing device for providing physical training functions.

Training system 100 may include a communication interface 130 to provide information exchange between controller 120 and sensor pad 110. Communication interface 130 may include a wired connection, e.g., via a hardware cable or wire, to provide a communication channel between controller 120 and sensor pad 110. The hardware cable may include general-purpose cables, such as USB cables. In some embodiments, the hardware cable may include some information processing functions. For example, the hardware cable may include built-in electronic chips to perform analog-to-digital signal conversion. In some embodiments, communication interface 130 may include a wireless connection, e.g., via WiFi, Bluetooth, infrared, RF, near field communication, etc., to provide a communication channel between controller 120 and sensor pad 110.

In some embodiments, such as during a training session, controller 120 may be placed on a supporting structure 140, such as a tripod, an that controller 120 can be held at a proper height to receive input from and provide feedback to the user. Supporting structure 140 may also include a rack, a cart, a hanging rod, or any other suitable means that can be used to hold controller 120 at a proper height. Supporting structure 140 may be adjustable, flexible, moveable, rotatable, etc.

In some embodiments, training system 100 may include a network interface 150 to connect controller 120 to a network 160. Network 160 may include LAN, WAN, telecommunication network, Internet, VPN, etc. Network interface 150 may include wired and/or wireless connections, such as WiFi, Ethernet, 3G, 4G, LTE, etc. Controller 120 may exchange information with other computers, such as servers or peers, through network 160.

In some embodiments, training system 100 may include a server 170 that connects to network 160. Server 170 may include a database 172 for storing data related to one or more users of training system 1100.

Figure 2:
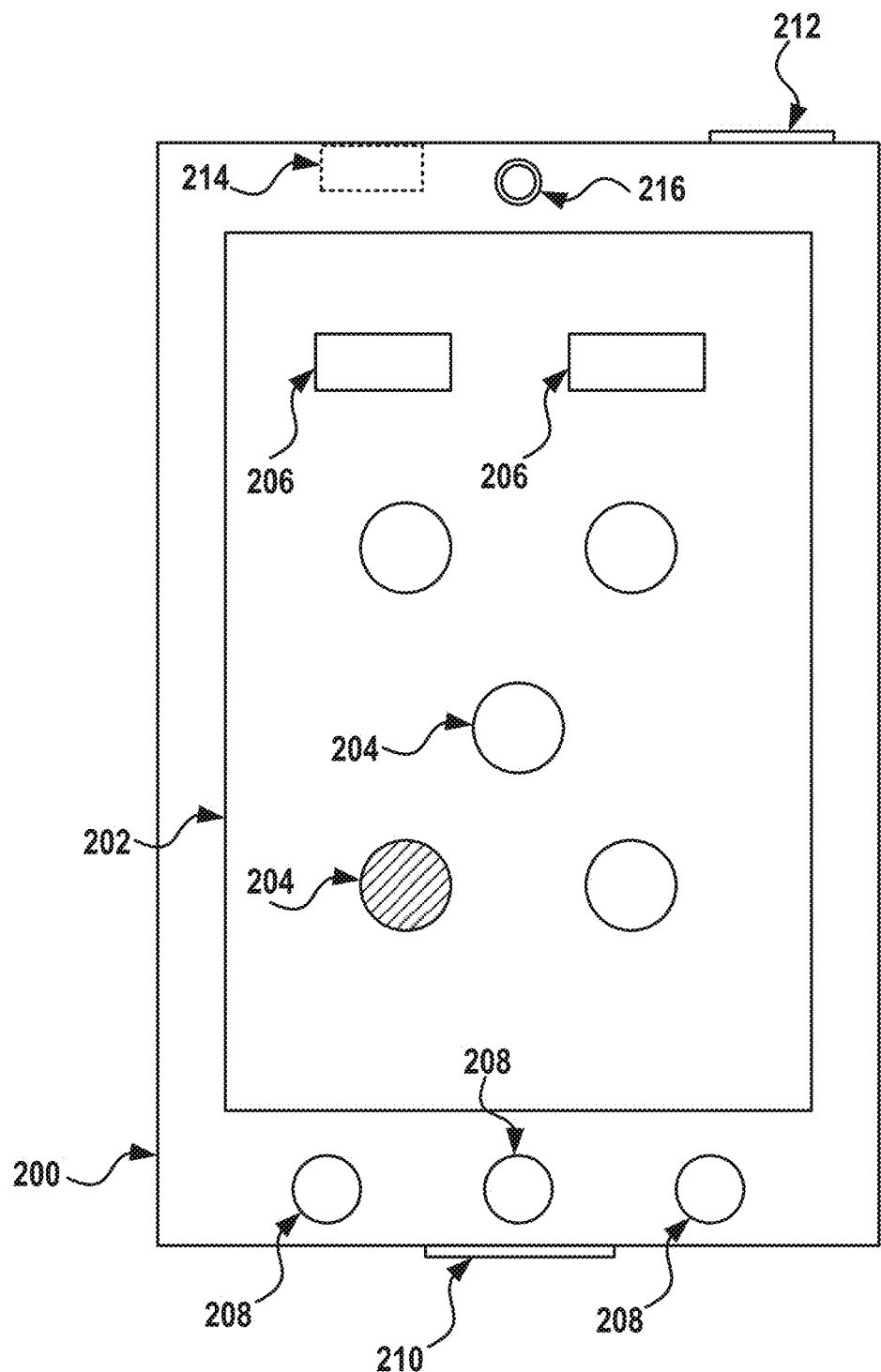
FIG. 2 is a schematic diagram of an exemplary controller, in accordance with some disclosed embodiments.

FIG. 2 illustrates an exemplary controller 200. As shown in FIG. 2, controller 200 may include a display panel 202. Display panel 202 may display video, image, and/or text information to a user. For example, display panel 202 may display one or more visual indicators 204. Visual indicator 204 may have various shapes (circle, square, triangle, etc), colors (yellow, red, green, blue, etc.), sizes, brightness, arrangements (different number of indicators in different row/column), etc. Visual indicator 204 may be individually rendered. For example, different visual indicators may have different colors, brightness, etc. Display panel 202 may also display one or more input buttons 206. In some embodiments, display panel 202 may include a touch-sensitive layer enabling controller 200 to receive input from a user when the user touches display panel 202.

Controller 200 may also include one or more hard buttons 208, a power switch 212, a connector interface 210, a build-in camera 216, and a wireless communication module 214. In some embodiments, connector interface 210 may be used to connect controller 200 to sensor pad 110 through cable 130. In some embodiments, wireless communication module 214 may be used to connect controller 200 to sensor pad 110 via, for example, Bluetooth, WiFi, etc. In some embodiments, wireless communication module 214 may be used to connect controller 200 to network 160 via, for example, WiFi, 3G, 4G, UTE, etc.

Figure 3:
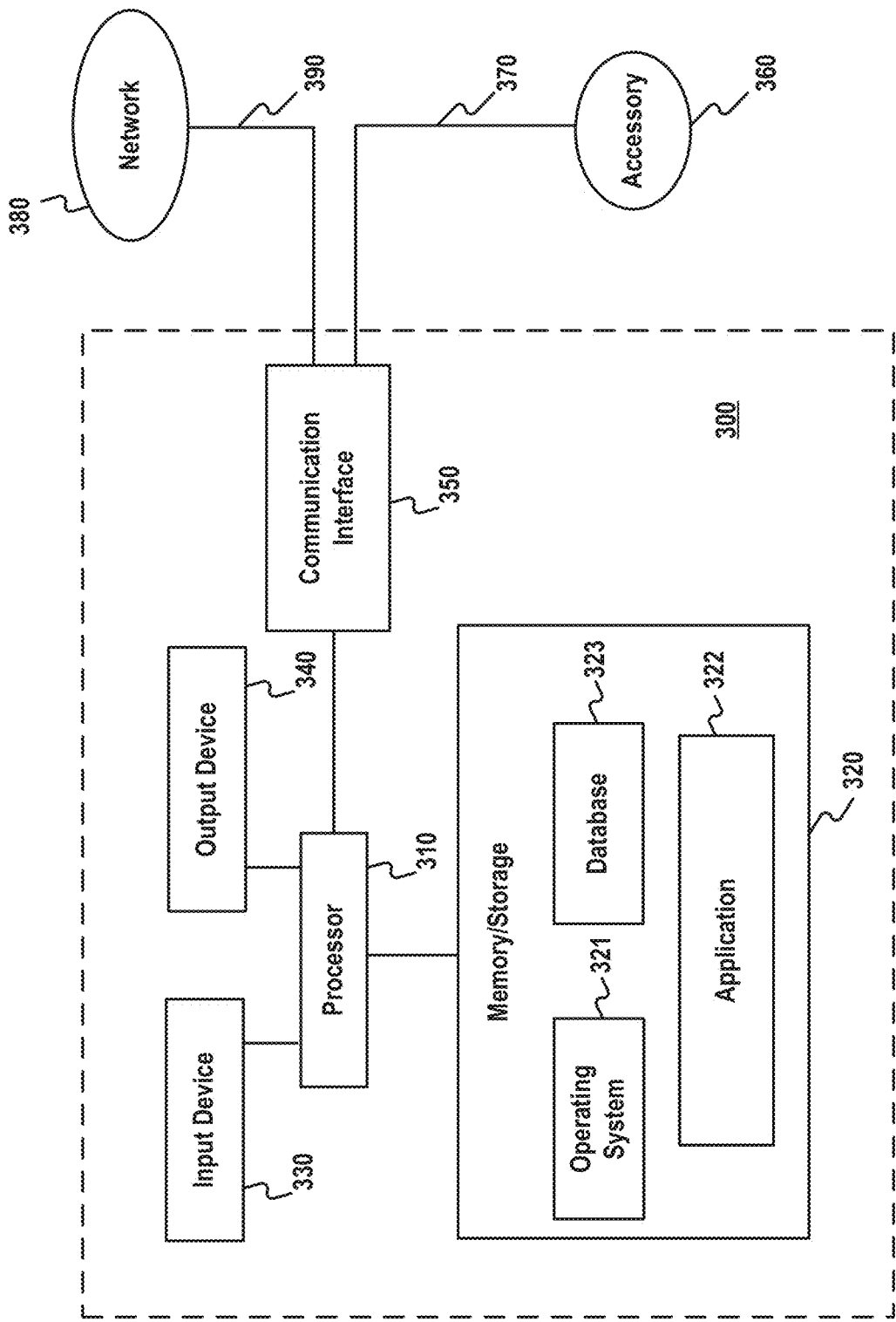
FIG. 3 illustrates a block diagram of an exemplary physical training system, in accordance with some disclosed embodiments.

FIG. 3 shows a block diagram of an exemplary physical training system. Consistent with some embodiments, the system may include a controller 300. Controller 300 may be a general purpose computer such as a laptop, a portable computing device such as a tablet or a mobile phone, or a computing device dedicated for physical training. As shown in FIG. 3, controller 300 may include a processor 310, a memory/storage module 320, a user input device 330, a display device 340, and a communication interface 350. Processor 310 can be a central processing unit ("CPU") or a mobile processor. Depending on the type of hardware being used, processor 310 can include one or more printed circuit boards, and/or a microprocessor chip. Processor 310 can execute sequences of computer program instructions to perform various methods that will be explained in greater detail below.

Memory/storage module 320 can include, among other things, a random access memory ("RAM"), a read-only memory ("ROM"), and a flash memory. The computer program instructions can be stored, accessed, and read from the ROM or flash, or any other suitable memory location, and loaded into the RAM for execution by processor 310. For example, memory/storage module 320 may store an operating system 321, a software application 322, and a database 323. Further, memory/storage module 320 may store an entire software application or only a part of a software application that is executable by processor 310.

In some embodiments, software application 322 or portions of it may be stored on a computer readable medium, such as a hard drive, computer disk, CD-ROM, DVD±R, CD±RW or DVD±RW, HD or Blu-ray DVD, flash drive, SD card, memory stick, or any other suitable medium, and can be read and acted upon by processor 310 using routines that have been loaded to memory/storage module 320.

In some embodiments, input device 330 and display device 340 may be coupled to processor 310 through appropriate interfacing circuitry. In some embodiments, input device 330 may be a hardware keyboard, a keypad, or a touch screen, through which a user may input information to controller 300. Display device 340 may include one or more display screens that display the training interface, result, or any related information to the user.

Communication interface 350 may provide communication connections such that controller 300 may exchange data with external devices. For example, controller 300 may be connected to network 380 through communication channel 390. Network 380 may be a LAN, a WAN, or the Internet. In some embodiments, controller 300 may be connected to an accessory 360 through communication channel 370. Accessory 360 may include, for example, sensor pad 110 or an external camera (not shown).

Figure 4A:
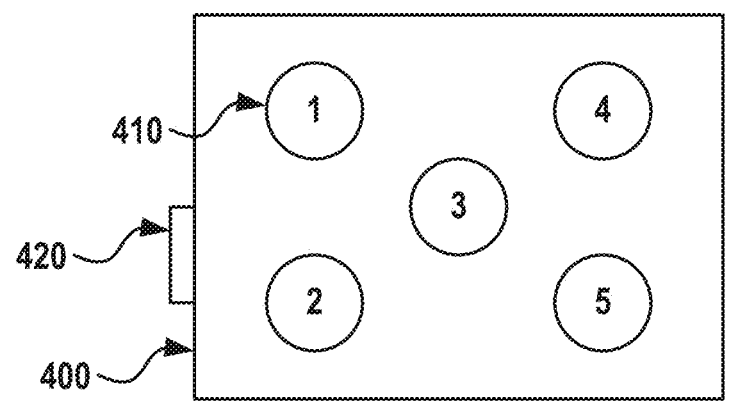
FIG. 4A is a schematic diagram of an exemplary sensor pad, in accordance with some disclosed embodiments.

FIG. 4A is a schematic diagram of an exemplary sensor pad, in accordance with some disclosed embodiments. Referring to FIG. 4A, sensor pad 400 may include a number of sensor units 410 and an interface 420. Sensor units 410 may be assigned predetermined identifiers, such as numbers 1-5, as illustrated in FIG. 4A. It is noted that different number of sensor units, different kinds of identifiers, and different manners of identifier assignment (e.g., the arrangement and order of the identifiers) may also be used. Sensor pad 400 may provide signals indicating whether a particular sensor unit is touched or pressed. In some embodiment, sensor pad 400 may also provide signals indicating the time duration of the pressure or force applied to the sensor pad 400. The signals may be sent to controller 120 (FIG. 1) through interface 420.

Figure 4B:
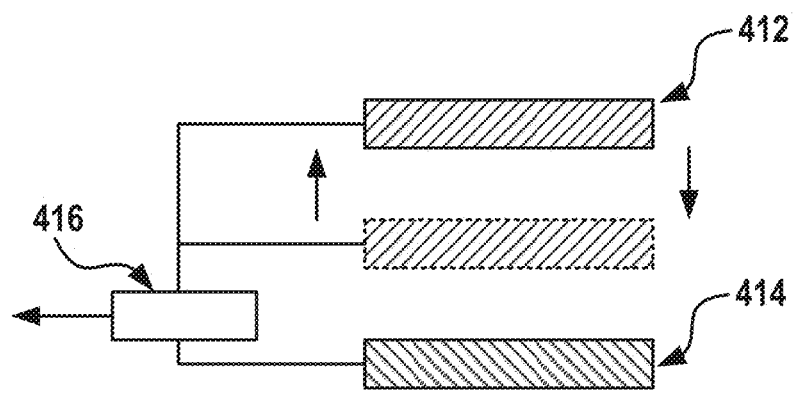
FIG. 4B is a schematic diagram of an exemplary sensor unit, in accordance with some disclosed embodiments.

FIG. 4B is a schematic diagram of an exemplary sensor unit, in accordance with some disclosed embodiments. In FIG. 4B, the sensor unit includes a top panel 412 and a bottom panel 414. When a user touches or presses the sensor unit, top panel 412 moves downward toward the dashed-line position. Such position change may lead to a change of resistance, which may be sensed by sensor 416. Sensor 416 may in turn generate a signal indicating that the sensor unit has been touched or pressed, based on the resistance change, and output the signal to interface 420 for communication with controller 120.

Figure 5:
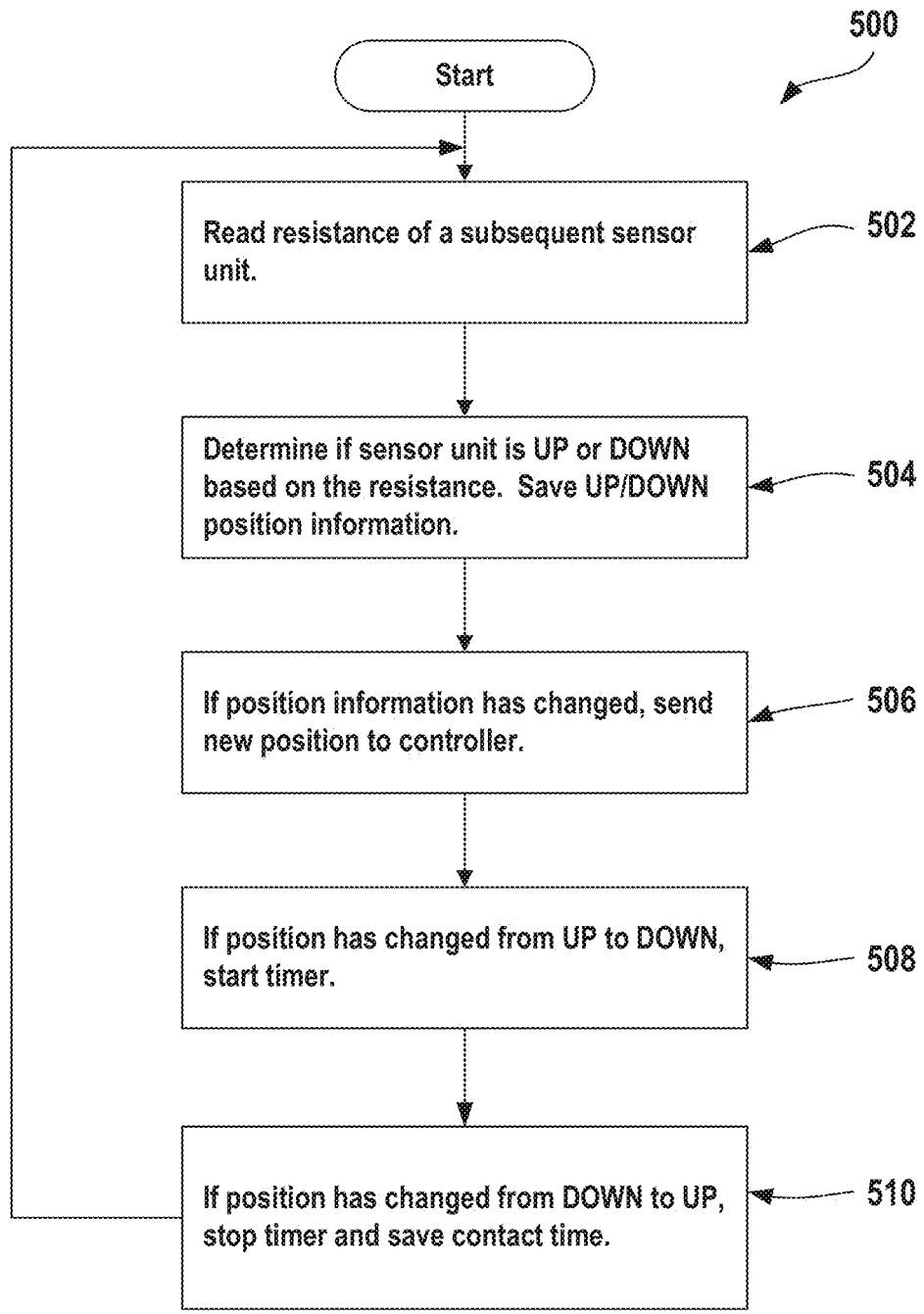
FIG. 5 is a flow chart of an exemplary method of determining time duration of touching a sensor unit, in accordance with some disclosed embodiments.

FIG. 5 is a flow chart of an exemplary method of determining time duration of touching a sensor unit, in accordance with some disclosed embodiments. As shown in FIG. 5, method 500 may include a series of steps, some of them may be optional. In step 502, sensor 416 reads resistance of a subsequent sensor unit. For example, as shown in FIG. 4A, the resistance of sensor units 1-5 may be read sequentially, and a next sensor unit may indicate, for example, sensor unit 5 after the steps described in FIG. 5 has finished a cycle for sensor unit 4. In step 504, the position of the sensor unit can be determined based on the resistance, For example, the resistance may be smaller when top panel 412 moves DOWN than when top panel 412 moves UP. The UP/DOWN position information can be saved. In step 506, it is determined if the position information has been changed, compared with the previously saved position information. If the position information has changed, the new position can be sent to controller 120. In step 508, it is determined if the position has changed from UP to DOWN. If so, the new position indicates that the sensor unit has been touched or pressed, and a timer can be adapted to measure the contact time. In step 510, it is determined if the position has changed from DOWN to UP. If so, the new position indicates that the sensor unit has been released. The timer can be stopped and the time duration of the pressure or force applied to the sensor unit, for example, can be saved. The process then returns to step 502 to read the next sensor unit (e.g., sensor unit 1). Method 500 may be initiated upon receiving a request from controller 120. Contact time information may be sent to controller 120, once available.

In some embodiments, software application 320 may include a plurality of pre-set drills for performing physical training Examples of pre-set drills may include count drills, react drills, sequence drills, vertical drills, and agility drills, as described herein. A user may also create a customized drill, a new category of drills, and/or a playlist of drills.

Count drills are designed to test and/or improve speed or quickness of movements. The user is instructed to perform pre-determined movements during count drills. In an exemplary count drill, controller 120 may activate one or more sensor units 112 (or all sensor units in some embodiments) on sensor pad 110. Controller 120 may record the total number of touches on the activated sensor units during specific time durations. Alternatively, controller 120 may record the time duration for finishing a pre-set number of touches. The goal of the user is to touch the activated sensor units as quickly as possible. When the user touches a sensor unit, the corresponding visual indicator may light up on display panel 202. The number of touches and/or the time (spending and/or remaining) can be displayed on display panel 202 in real time. The user may be able to choose or program the pre-determined movements (e.g., type or manner of movements, sensor units to be activated, specific order of touches, etc.), number of touches to be accomplished, and/or me duration of the drill. In another example, the user can stand on the front or back two sensor units (e.g., 1 and 2 or 4 and 5 in FIG. 4A), and controller 120 may activate the two sensor units as a left and a right touch target. The number of left and right touches can be displayed separately on display panel 202 in real time. The time (spending and/or remaining) can also be displayed on display panel 202. Contac time may also be determined by, for example, method 500 illustrated in FIG. 5.

React drills are designed to test and/or improve a user's speed of reaction to visual indicators 204 displayed on display panel 202. In an exemplary react drill, a sequence of visual indicators 204 can be programmed to be displayed on display panel 202, and a user needs to react to the visual indicators 204 and perform a series of movements, e.g., by touching the corresponding sensor units 112 on sensor pad 110. In some embodiments, the visual indicators can be assigned a certain color, and the user is instructed to react to the visual indicators with the assigned color. In some embodiments, the visual indicators can be assigned different colors, and the user is instructed to react to certain colors, but not others. The user reacts to the visual indicator by touching the corresponding sensor unit as quickly as possible. If the user correctly touches the corresponding sensor unit, controller 120 may receive a signal from sensor pad 110 indicating a corresponding sensor unit has been touched. Controller 120 may then determine that the user has completed the expected movement and record a correct touch. If the user touches an incorrect sensor unit that does not correspond to the "react to" visual indicator, or the user touches a sensor unit corresponding to a "don't react to" visual indicator, or the user fails to touch the corresponding sensor unit fast enough (e.g., the reaction/response time is longer than a predetermined threshold), controller 120 may determine that the user does not complete the expected movement and record an incorrect touch. The total number of correct touches and the total number of incorrect touches can be displayed on display panel 202 in real time. The time (spending and/or remaining) can also be displayed on display panel 202. In some embodiments, response times may also be recorded. The response time may be measured from the time the visual indicator first appears on display panel 202 to the time when the sensor unit (either a correct or an incorrect one) senses the responding/reacting touch. Contact time may also be determined by, for example, method 500 illustrated in FIG. 5.

The sequence of visual indicators in react drills may be randomly generated. In some embodiments, controller 120 may be configured such that the same order of visual indicators in a random sequence is not repeated.

Visual indicators may be displayed in different manners, For example, the visual indicator may display in a solid mode, in which the visual indicator is being displayed until the user touches a sensor unit. In another example, the visual indicator may display a flash mode, in which the visual indicator illuminates for a pre-determined duration (e.g., 0.10 to 10.0 seconds in increments of 0.10 seconds) and then disappears, regardless of whether the user touches a sensor unit during this time duration. If the user fails to touch the corresponding sensor unit during the pre-determined time duration, the failure to touch will be treated as an incorrect touch or an incomplete movement.

In some embodiments, the react drill may include a flip mode. In the flip mode, the user is instructed to react to the opposite sensor corresponding to the displayed visual indicator. In one embodiment, the user may be instructed to react to a diagonally opposite sensor. For example, if the top right visual indicator appears on the display panel, the user should react to the sensor unit on the bottom left. In another embodiment, the user may be instructed to react to a lateral opposite sensor. For example, if the top right visual indicator appears on the display panel, the user should react to the top left sensor unit. In yet another embodiment, the user may be instructed to react to a linear opposite sensor. For example, if the top right visual indicator appears on the display panel, the user should react to the bottom right sensor unit.

Sequence drills are similar to react drills. One of the differences is that instead of random sequences, pre-determined sequences of visual indicators are used in sequence drills. The pre-determined sequences can be generated by the software application or by the user. The user may setup a sequence by inputting a series of numbers indicating the corresponding sensor units. The total number of sensor units in a sequence may vary. For example, in some embodiments, the total number may be from 1-20. In sequence drills, the number of correct and incorrect touches can also be provided and displayed on display panel 202 in real time, similar to that of the react drills. The time (spending and/or remaining) can also be displayed on display panel 202. Contact time may also be determined by, for example, method 500 illustrated in FIG. 5.

In both react and sequence drills, a time delay can be set between the appearance of a visual indicator and the receiving of a user response (e.g., a correct touch or an incorrect touch). For example, a 2-3 seconds delay may be added before the user responds to the visual indicator.

After a user finishes a drill, controller 120 may save result of the drill. In some embodiments, controller 120 may provide comparative data about the current result and previous results of the user, thereby showing whether the user's performance has been improved over time. The comparative data may be displayed on display panel 202 using a tabular view and/or a graphical view. The tabular view may include percentage improvement or decrease, in addition to current result and past results. The graphical view may include bar/circle/curve graphical representations of the results comparisons.

Drills may be performed using either lower limbs (legs) or upper limbs (hands). In lower limb mode, sensor board 110 can be used to sense the user's movements/touches. In upper limb mode, the user may perform the drill by touching display panel 202 directly using his/her fingers.

Figure 6:
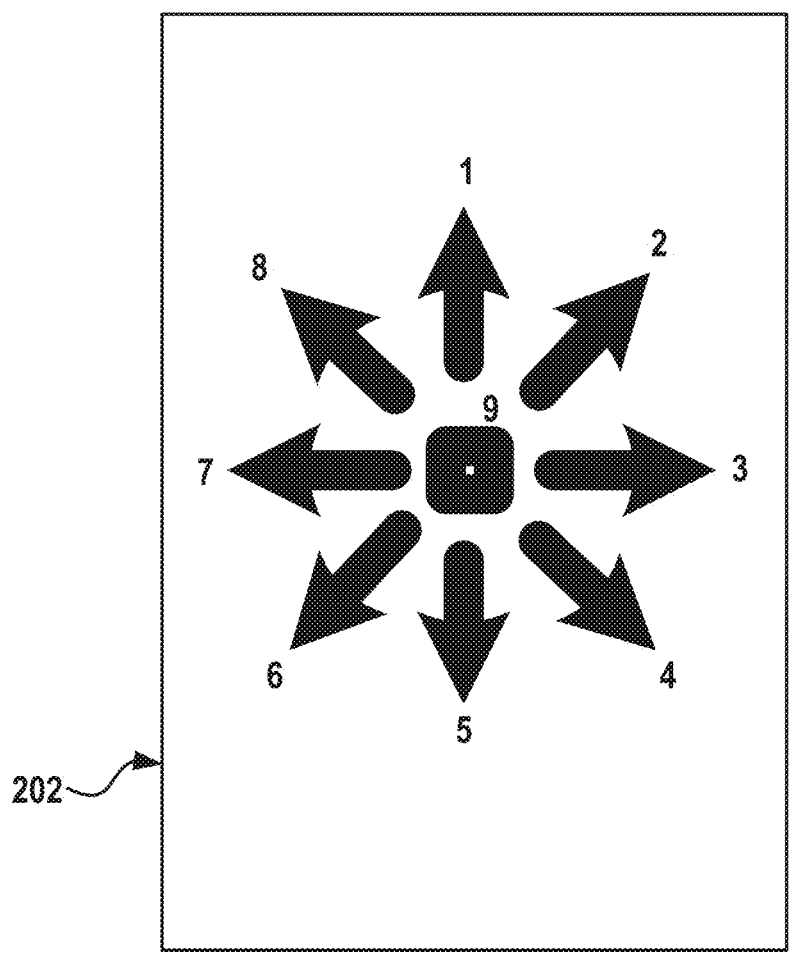
FIG. 6 shows an exemplary setup screen for performing an agility drill, in accordance with some disclosed embodiments.

Agility drills may be performed to test and/or improve the agility of a user. In an agility drill, the user responds to a sequence of arrows displayed on display panel 202 and moves in the direction of the arrow. FIG. 6 shows an exemplary setup screen for performing an agility drill in an arrow sequence mode. In FIG. 6, eight arrows represent eight directions identified by numbers 1 to 8. In the arrow sequence mode, the user is able to program the sequence of the drill by inputting the sequence of numbers. Number 9 can be used as a wild card. Alternatively, in an arrow react mode, arrows may appear randomly.

The length of the agility drill can be programmed by time (e.g., 1 second to 60 mins) or by arrow count (e.g., 1 to 20 arrows). The delay time between the appearing of two adjacent arrows can also be programmed (e.g., from 1 to 20 seconds with incremental of 0.5 second).

Vertical drills may be performed to assess height of a user's jump. In a vertical drill, the user stands on one or more of the sensor units, jumps, and lands on the same sensor unit. Controller 120 can detect the duration of time between the user's lift off from the sensor unit (e.g., sensor unit released) and the user's next contact with the sensor unit (e.g., sensor unit compressed again). Contact time may also be determined by, for example, method 500 illustrated in FIG. 5. Body weight of the user can be taken into account to improve accuracy. Similar to those of count drills, the number of jumps and the time (spending and/or remaining) can be displayed on display panel 202 in real time.

For every type of drills, the user can program the length of the drill by specify either the time duration of the drill or the target number of touches. The target number of touches may include the number of correct touches. the number of total touches (both correct and/or incorrect), or the number of visual indicators appearing on the display panel.

Videos of a user performing a drill can be recorded. For example, a video can be recorded using camera 216 (FIG. 2) that is equipped with controller 120. The recorded video may be provided to the user along with other performance data collected, for example, from sensor pad 110.

in some embodiments, sensor pad 110 may be replaced by a high speed camera. For example, the high speed camera may he set up to synchronize with controller 120 to monitor the user performing a drill. The user can place any type of targets on the ground, e.g., a rubber mat, rubber dots, spray painted dots, etc., for the high speed camera to capture and register the user's touch/contact actions or movements. In some embodiments, the camera can be used for gait testing and analysis, training and rehabilitation for high performance athletes, or general rehabilitation patients.

In some embodiments, a user may create a use profile. The user profile may include use data such as name, gender, age, height, weight, sports, position, injuries, etc. Performance data and videos of pre-set and customized drills may be saved based on user profiles. In some embodiments, performance data may be exported (e.g., as .csv files).

in some embodiments, an online database (e.g., database 172) may be provided to users (e.g., for an annual fee or other suitable fee structures). The database may allow users to upload their saved drill results for comparison with other users. Databases can be developed for the general consumers, high school sports teams, collegiate sports teams, professional teams, Olympic athletes, physical therapy clinics, sports medicine clinics, etc. Controller 120 may upload saved drill results and the user profile data in order to compare the results. A user profile may include fields for segregating, filtering, or targeting certain user information, such as sports, position, professional level, demographic information to specific drills data and settings. Drills listed in the online database may contain demo videos to display how the drills should be performed.

Exemplary online databases include: (1) a performance database for individuals, high schools and colleges to compare results to other users around the world; (2) a rehabilitation database for physical therapy clinics, collegiate/professional sports medicine staffs and sports medicine clinics; and (3) a high level athletic performance and rehabilitation database for professional sports teams or Olympic level training facilities that includes normative data of athletes who possess similar performance abilities. The high level database may isolate normative data from professional leagues, e.g., NBA, NFL, MLB, NHL, etc.

In the foregoing description of exemplary embodiments, various features are grouped together in a single embodiment for purposes of streamlining the disclosure. This method of disclosure is not to be interpreted as reflecting an intention that the claims require more features than are expressly recited in each claim. Rather, as the following claims reflect, inventive aspects lie in less than all features of a single foregoing disclosed embodiment. Thus, the following claims are hereby incorporated into this description of the exemplary embodiments, with each claim standing on its own as a separate embodiment of the invention.

Moreover, it will be apparent to those skilled in the art from consideration of the specification and practice of the present disclosure that various modifications and variations can be made to the disclosed systems and methods without departing from the scope of the disclosure, as claimed. Thus, it is intended that the specification and examples be considered as exemplary only, with a true scope of the present disclosure being indicated by the following claims and their equivalents.

What is claimed is:

1. A system for providing a physical training routine for testing and improving a user's speed of reaction by administering reaction or agility drills, the system comprising:
   a memory for storing a set of instructions;
   a sensor pad including a plurality of sensor units for registering foot touches by said user, the plurality of sensor units including a center sensor unit and at least four peripheral sensor units spaced peripherally from the center sensor unit;

a controller operatively connected to the sensor units of the sensor pad, the controller including a display panel, the display panel configured to display a plurality of visual indicators, each of the visual indicators arranged to correspond to a position of one of the sensor units for use in directing said user to touch a sequence of sensor units, and the controller including a processor communicatively connected to the memory, wherein the set of instructions, when executed by the processor, cause the processor to perform operations including:

controlling the display panel to display a sequence of visual indicators on the display panel, each display of a visual indicator indicating a sensor unit for said user to touch, determining performance data indicating an agility of said user in practicing a movement, including:

receiving, in response to each display of a visual indicator, a signal from a corresponding sensor pad indicating that a touch action by said user is received by an individual sensor unit;

displaying, in response to each successful touch action, a subsequent visual indicator in the sequence, wherein each display of a visual indicator in response to a touch action is initiated by said user touching a sensor unit, rather than by the controller, recording the performance data in the memory;

associating the recorded performance data with a user profile of said user, the user profile including gender, sports, and injury data of the user for segregating, filtering, or targeting user information relating to said user;

uploading the recorded performance data to an online database for comparison with a group of other users based on the user profile;

accessing normative data stored in the online database, the normative data including performance data of athletes possessing similar performance abilities to said user; and comparing the performance data of said user with performance data of the athletes possessing similar performance abilities to said user for training, testing, and rehabilitation for said user;

wherein the sensor pad is configured to:

generate the signal indicating that the touch action is received by the individual sensor unit based on a change of a resistance of the individual sensor unit.

2. The system of claim 1, wherein determining performance data indicating a reaction of said user in performing touch actions includes:

receiving, from the sensor pad, contact time information indicating a time duration of the touch action;

determining the performance data based on analysis of the signal and the contact time information to determine the time duration of the touch action by:

reading the resistance of the individual sensor unit;

determining a position of the sensor unit based on the resistance;

saving the position;

determining a position change by comparing the determined position and a previously saved position;

starting a timer when it is determined that the position of the sensor unit changes from an up position to a down position;

stopping the timer when it is determined that the position of the sensor unit changes from the down position to the up position; and determining the time duration of the touch action based on the timer; and sending the signal indicating that the touch action is received by the individual sensor unit and the contact time information indicating the time duration of the touch action to the processor.

3. The system of claim 1, wherein the operations include:

determining whether the user completes a sequence of movements corresponding to the sequence of visual indicators displayed on the visual display;

recording one or more characteristics of the sequence of movements; and providing feedback to the user based on the one or more characteristics.

4. The system of claim 3, wherein the sequence of movements is a predetermined sequence.

5. The system of claim 3, wherein the one or more characteristics include at least one of a total number of completed movements or a total number of incomplete movements.

6. The system of claim 1, wherein the performance data include a response time between displaying the visual indicator and completion of the movement.

7. The system of claim 1, further comprising the online database, wherein the online database is configured to isolate the normative data from professional leagues and compare the normative data among users possessing similar performance abilities.

8. The system of claim 1, wherein the processor is further configured to execute the set of instructions to perform a vertical drill to determine a height of a jump conducted by the user, including:

receiving a first signal from the sensor pad indicating a sensor unit release action when the user jumps off the sensor pad;

receiving a second signal from the sensor pad indicating a sensor pad compress action when the user lands on the sensor pad;

determining a lift off time duration based on the first and second signal; and determining a height of the jump based on the lift off time duration.

9. A method for providing a physical training routine for testing and improving a user's speed of reaction by administering reaction or agility drills, comprising:

providing a sensor pad including a plurality of sensor units for registering foot touches by said user, the plurality of sensor units including a center sensor unit and at least four peripheral sensor units spaced peripherally from the center sensor unit;

determining, by a processor, performance data indicating an agility of said user in practicing a movement, including:

controlling a display panel to display a plurality of visual indicators indicating the movement to be completed by said user, each of the visual indicators arranged to correspond to a position of one of the sensor units for use in directing said user to touch a sequence of sensor units;

receiving, in response to each display of a visual indicator, a signal from a corresponding sensor pad indicating that a touch action by said user is received by an individual sensor unit displaying, in response to each successful touch action, a subsequent visual indicator in the sequence, wherein each display of a visual indicator in response to a touch action is initiated by said user touching a sensor unit, rather than by the controller;

determining, by the processor, the performance data based on analysis of the signal; and recording, in a memory, the performance data;

associating the recorded performance data with a user profile of the user, the user profile including gender, sports, and injury data of the user for segregating, filtering, or targeting user information relating to the user;

uploading the recorded performance data to an online database for comparison with a group of other users based on the user profile;

accessing normative data stored in the online database, the normative data including performance data of athletes possessing similar performance abilities to the user;

comparing the performance data of the user with performance data of the athletes possessing similar performance abilities to the user for training, testing, and rehabilitation for the user;

generating, by the sensor pad, the signal indicating that the touch action is received by the individual sensor unit based on a change of a resistance of the individual sensor unit.

10. The method of claim 9, wherein the signal indicates whether the user touches an area of the sensor pad corresponding to the visual indicator.

11. The method of claim 9, wherein determining performance data indicating a reaction of a user in performing touch actions includes:
determining the time duration of the touch action by:
reading the resistance of the individual sensor unit;
determining a position of the sensor unit based on the resistance;
saving the position;
determining a position change by comparing the determined position and a previously saved position;
starting a timer when it is determined that the position of the sensor unit changes from an up position to a down position;
stopping the timer when it is determined that the position of the sensor unit changes from the down position to the up position; and
determining the time duration of the touch action based on the timer; and
sending, by the sensor pad, the signal indicating that the touch action is received by the individual sensor unit and the contact time information indicating the time duration of the touch action to the processor.

12. The method of claim 9, further comprising:
determining whether the user completes a sequence of movements corresponding to the sequence of visual indicators displayed on the visual display;
recording one or more characteristics of the sequence of movements; and
providing feedback to the user based on the one or more characteristics.

13. The method of claim 12, wherein the sequence of movements is a predetermined sequence.

14. The method of claim 12, wherein the one or more characteristics include at least one of a total number of completed movements or a total number of incomplete movements.

15. The method of claim 9, wherein the performance data include a response time between displaying the visual indicator and completion of the movement.

16. A non-transitory computer-readable medium encoded with software code instructions, when executed by a processor, implementing a method for providing a physical training routine for a user, the method comprising:
determining performance data indicating an agility of the user in practicing a movement, including:
displaying a sequence of visual indicators on a display panel, the sequence of visual indicators indicating a sequence of movements to be completed by said user, wherein each display of a visual indicator in the sequence is initiated by said user touching a sensor unit rather than by the processor;
receiving, from a sensor pad, a signal indicating that a touch action is received by an individual sensor unit, the sensor pad including a plurality of the sensor units for registering foot touches by said user, the plurality of sensor units including a center sensor unit and at least four peripheral sensor units spaced peripherally from the center sensor unit, and the display panel configured to display a plurality of visual indicators, each of the visual indicators arranged to correspond to a position of one of the sensor units for use in directing said user to touch a sequence of sensor units;
determining, by the processor, the performance data based on analysis of the signal information; and
recording, in a memory, the performance data;
associating the recorded performance data with a user profile of the user, the user profile including gender, sports, and injury data of the user for segregating, filtering, or targeting user information relating to the user;
uploading the recorded performance data to an online database for comparison with a group of other users based on the user profile;
accessing normative data stored in the online database, the normative data including performance data of athletes possessing similar performance abilities to the user;
comparing the performance data of the user with performance data of the athletes possessing similar performance abilities to the user for training, testing, and rehabilitation for the user;
generating, by the sensor pad, the signal indicating that the touch action is received by the individual sensor unit based on a change of a resistance of the individual sensor unit.

17. The computer-readable medium of claim 16, wherein the performance data include a response time between displaying the visual indicator and completion of the movement.

18. The computer readable medium of claim 16, further comprising performance data including receiving, from the sensor pad, contact time information indicating a time duration of the touch action;
determining the time duration of the touch action by:
reading the resistance of the individual sensor unit;
determining a position of the sensor unit based on the resistance;
saving the position;

determining a position change by comparing the determined position and a previously saved position;
starting a timer when it is determined that the position of the sensor unit changes from an up position to a down position;
stopping the timer when it is determined that the position of the sensor unit changes from the down position to the up position; and
determining the time duration of the touch action based on the timer; and sending, by the sensor pad, the signal indicating that the touch action is received by the individual sensor unit and the contact time information indicating the time duration of the touch action to the processor.

* * * * *